(12) United States Patent
Yeh et al.

(10) Patent No.: US 7,438,980 B2
(45) Date of Patent: Oct. 21, 2008

(54) ORGANOMETALLIC COMPLEX AND ORGANIC ELECTROLUMINESCENT DEVICES UTILIZING THE SAME

(75) Inventors: Shu-Tang Yeh, Taichung County (TW); Tien-Shou Shieh, Taipei (TW); Mei-Rurng Tseng, Hsinchu (TW); Miao-Tsai Chu, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 535 days.

(21) Appl. No.: 11/176,274

(22) Filed: Jul. 8, 2005

(65) Prior Publication Data

US 2006/0134462 A1    Jun. 22, 2006

(30) Foreign Application Priority Data

Dec. 22, 2004    (TW)    ............................... 93140052 A

(51) Int. Cl.
*H01L 51/54*    (2006.01)
*C09K 11/06*    (2006.01)
(52) U.S. Cl. .................. 428/690; 313/504; 313/506; 257/40; 257/E51.044; 544/225
(58) Field of Classification Search ............... 546/4, 546/10; 544/225; 549/3; 428/690, 917; 313/504, 506; 257/40, E51.044
See application file for complete search history.

(56) References Cited

U.S. PATENT DOCUMENTS

| | | | |
|---|---|---|---|
| 2001/0019782 A1* | 9/2001 | Igarashi et al. ............... | 428/690 |
| 2002/0024293 A1 | 2/2002 | Igarashi et al. | |
| 2002/0034656 A1 | 3/2002 | Thompson et al. | |
| 2003/0017361 A1 | 1/2003 | Thompson et al. | |
| 2003/0068526 A1* | 4/2003 | Kamatani et al. ........... | 428/690 |
| 2003/0072964 A1* | 4/2003 | Kwong et al. ............... | 428/690 |
| 2004/0241495 A1* | 12/2004 | Kwong et al. ............... | 428/690 |
| 2004/0247934 A1* | 12/2004 | Takeuchi et al. ............ | 428/690 |

FOREIGN PATENT DOCUMENTS

EP    1 434 286 A1    6/2004

* cited by examiner

*Primary Examiner*—Callie Shosho
*Assistant Examiner*—Michael Wilson
(74) *Attorney, Agent, or Firm*—Birch, Stewart, Kolasch & Birch, LLP

(57) ABSTRACT

An organometallic complex is provided. The organometallic complex is selected from the group consisting of -continued
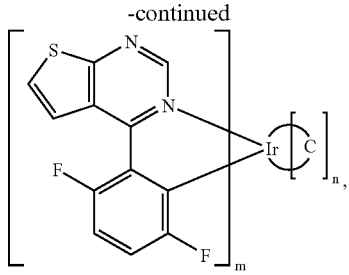
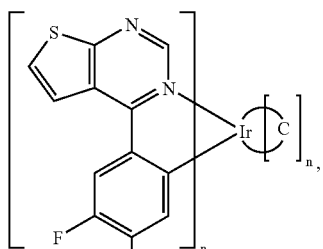
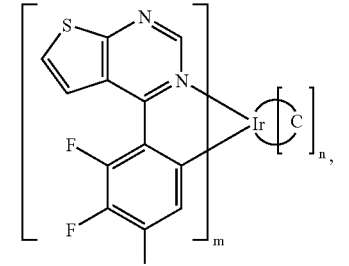
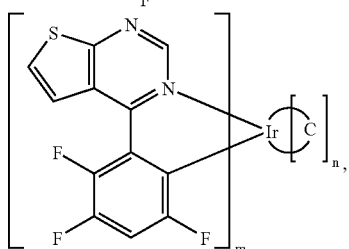
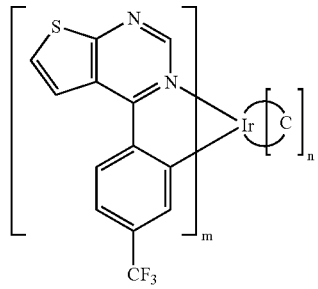
and
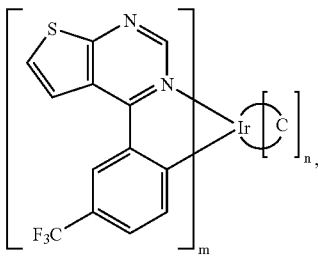
wherein C is an acetyl acetone group
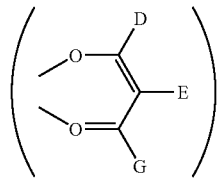
or picolinic acid group
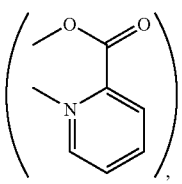
m is 1~3, n is 0~3 and m+n=3, wherein D, E and G are the same or different and selected from the group consisting of H, halogen atoms, trifluoromethyl, $C_{1-20}$ alkyl, $C_{1-20}$ alkyl halide, $C_{3-10}$ aryl and $C_{3-20}$ heterocyclic ring containing O, N or S.
26 Claims, 1 Drawing Sheet

ORGANOMETALLIC COMPLEX AND ORGANIC ELECTROLUMINESCENT DEVICES UTILIZING THE SAME

BACKGROUND

The present invention relates to an organometallic complex, and more specifically to an organometallic complex used in an organic electroluminescent device.

Organic electroluminescent devices are popular in flat panel display due to their high illumination, light weight, self-illumination, low power consumption, simple fabrication, rapid response time, wide viewing angle, and no backlight requirement.

When an external electric field is applied to an organic electroluminescent device, electrons and holes are injected from cathode and anode, respectively, and then recombined to form excitons. Energy is further transported from excitons to luminescent molecules with continuous application of an electric field. Finally, luminescent molecules emit light converted from energy. A common organic electroluminescent device structure comprises an ITO anode, a hole transport layer, an emitting layer, a hole blocking layer, an electron transport layer, and a cathode. A complex organic electroluminescent device, however, may further comprise a hole injection layer disposed between an anode and a hole transport layer or an electron injection layer disposed between a cathode and an electron transport layer to improve injection efficiency of carriers, reducing driving voltage or increasing recombination thereof.

After a luminescent molecule absorbs specific energy, potential energy of electrons in an excited state may be released through fluorescence and phosphorescence. Fluorescence is produced by return of electrons from singlet excited state to ground state. Phosphorescence, however, is produced during a return of triplet excited state to ground state. In a fluorescent electroluminescent device, although 75% excitons arrive at triplet excited state, their potential energy cannot be released through emission light. Thus, only 25% internal quantum efficiency can be acquired, significantly reducing external quantum efficiency to lower than 5%. Nevertheless, in phosphorescent materials, potential energy of excitons in triplet excited state can be fully released through emission light, increasing internal quantum efficiency from 25% to 100%. Phosphorescent luminescent materials are composed of dopants and hosts, wherein dopants containing heavy atoms are preferable. Due to strong spin-orbital coupling from heavy atoms, singlet and triplet orbits can be effectively hybridized, increasing transition probability of excitons between singlet and triplet excited state and reducing half-life of excitons in triplet state. Thus, phosphorescent luminescent materials exhibit four times the luminescence of fluorescents.

Currently, red fluorescent materials comprise DCJTB (Kodak) or Pl (Idemitsu). The initial red fluorescent dopant developed from Kodak Corporation is DCM with luminescent efficiency of 78% and wavelength of 596nm, and its wavelength may alter with doping concentration. The optimal doping concentration is about 0.5%, and luminescent efficiency may achieve 2.3%. Unfortunately, DCM emits orange light, not the red light required. Also Kodak Corporation provides DCM-2 and DCJTB with increased steric hindrance, albeit with emission light still orange. Kodak Corporation further provides an electroluminescent device comprising DCJTB as well as a yellow luminescent dopant, Rubrene, to increase energy transfer efficiency and shift luminescent wavelength to the red light region. Nevertheless, the fabrication thereof is complicated. The optimal luminescent efficiency of related red fluorescent materials is merely 31 m/W with lifetime thereof also merely 10000 hours. Thus, development of red phosphorescent materials is desirable. Presently, a preferable red phosphorescent material is 2,3,7,8,12,13,17,18-octaethyl-12H,23Hporphine-platinum(II) (PtOEP) with wavelength of 650 nm, luminescent efficiency of 2.41 lm/W, a CIEx value of 0.7, a CIEy value of 0.3, and lifetime exceeding 8000 hours. Although luminescent characteristics of PtOEP are acceptable, applications thereof are limited due to complicated preparation and high cost. Thompson and Forrest provide another red phosphorescent material, bis(2-(2'-benzo[4,5-a]thienyl)pyridinato-N,$C^{3'}$)iridium(acetylacetonate) [$Btp_2Ir(acac)$], with luminescent efficiency of 4.71 lm/W, wavelength of 610 nm, a CIEx value of 0.67, and a CIEy value of 0.33. This material, however, still emits red-orange light.

As well as PtOEP and $Btp_2Ir(acac)$, other phosphorescent materials have been provided. As disclosed in E.P. Pat. No. 1434286, A Ir complex with various coordination groups is provided, comparing effects of various coordination groups on luminescent characteristics such as luminescent wavelength and efficiency. As disclosed in U.S. Pre-Grant Pat. No. 2002024293, a blue phosphorescent Ir complex with a luminescent wavelength greater than 500 nm and external quantum efficiency exceeding 5% is provided. As disclosed in U.S. Pre-Grant Pat. No. 2002034656 and 2003017361, Ir complexes with luminescent wavelengths 425 nm, 475 nm, 500 nm, 575 nm, and 615 nm distributing from blue to red-orange light regions is provided.

SUMMARY

The invention provides an organometallic complex having formula (I):

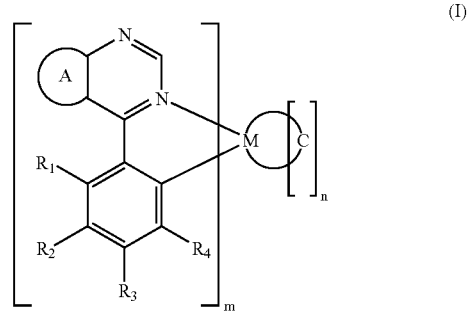

(I)

wherein M is a transition metal comprising Ir, Pt, Pd, or Rh, A is a $C_{3-20}$ aryl, $C_{3-20}$ cycloalkyl, or $C_{3-20}$ heterocyclic ring containing O, N, or S, $R_1$~$R_4$ are the same or different and comprise H, halogen atoms, trifluoromethyl, $C_{1-10}$ alkyl, $C_{3-10}$ aryl, $C_{3-10}$ cycloalkyl, or $C_{3-10}$ heterocyclic ring containing O, N, or S, C is an acetyl acetone group

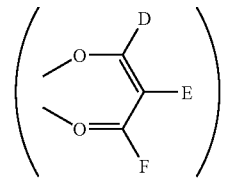

or picolinic acid group

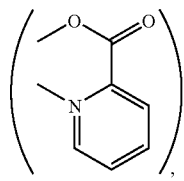

wherein D, E, and F are the same or different and comprise H, halogen atoms, trifluoromethyl, $C_{1-20}$ alkyl, $C_{1-20}$ alkyl halide, $C_{3-10}$ aryl, or $C_{3-20}$ heterocyclic ring containing O, N, or S, and when M is Ir or Rh, m is 1~3, n is 0~3, and m+n=3 and when M is Pt or Pd, m is 1~2, n is 0~2, and m+n=2.

The invention also provides an organic electroluminescent device comprising a pair of electrodes and an organic electroluminescent layer installed therebetween, utilizing the disclosed organometallic complex.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION

Figure 1:
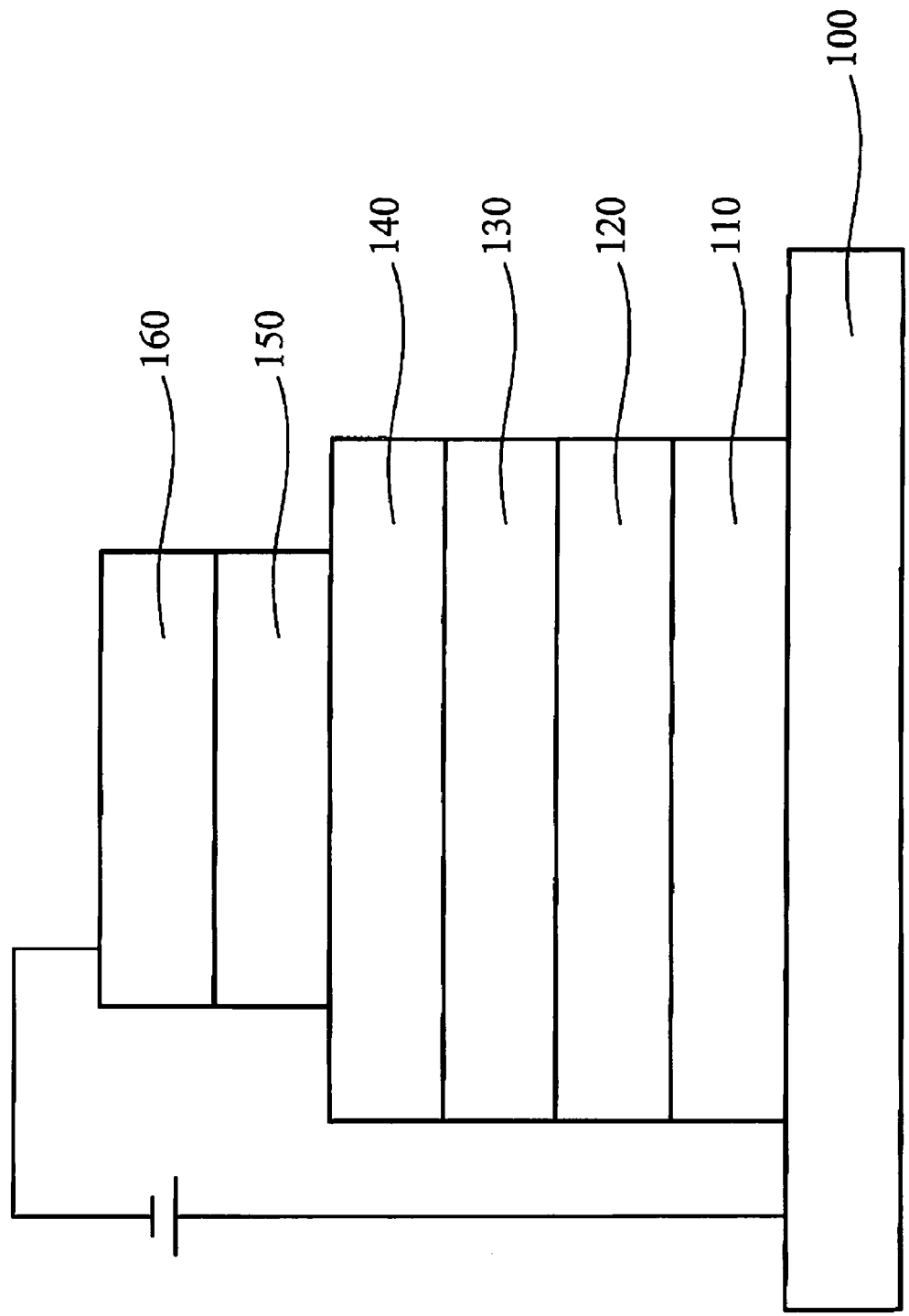
FIG. 1 is a cross section of an organic electroluminescent device of the invention.

The invention provides an organometallic complex having formula (I):

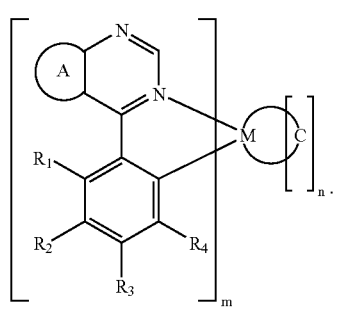

In formula (I), M is a transition metal with $d^6$ electron orbits such as Ir, Pt, Pd, or Rh, preferably Ir. A is a $C_{3-20}$ aryl, $C_{3-20}$ cycloalkyl, or $C_{3-20}$ heterocyclic ring containing O, N, or S, preferably phenyl or heterocyclic ring containing S.

$R_1$~$R_4$ are the same or different and comprise H, halogen atoms, trifluoromethyl, $C_{1-10}$ alkyl, $C_{3-10}$ aryl, $C_{3-10}$ cycloalkyl, or $C_{3-10}$ heterocyclic ring containing O, N, or S, preferably F atom or trifluoromethyl. C is an acetyl acetone group

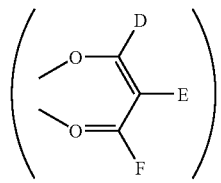

or picolinic acid group

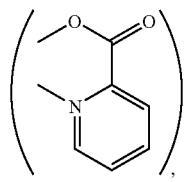

wherein D, E, and F are the same or different and comprise H, halogen atoms, trifluoromethyl, $C_{1-20}$ alkyl, $C_{1-20}$ alkyl halide, $C_{3-10}$ aryl, or $C_{3-20}$ heterocyclic ring containing O, N, or S, such as methyl, ethyl, isopropyl, sec-butyl, tert-butyl, phenyl, thiophenyl, benzothiophenyl, furanyl, napthalenyl, or pyridinyl. When M is Ir or Rh, m is 1~3, n is 0~3, and m+n=3. When M is Pt or Pd, m is 1~2, n is 0~2, and m+n=2.

The specific organometallic complexes provided by the invention are divided into three groups (1)~(3) with different coordination groups:

(1) 4-phenyl quinazoline coordination group:

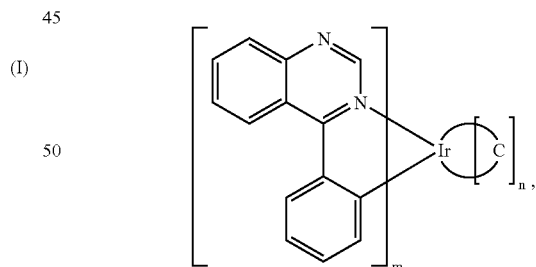

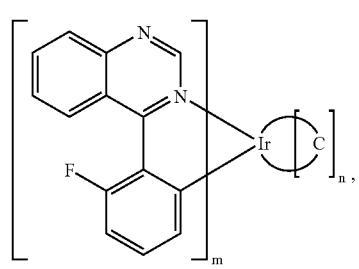

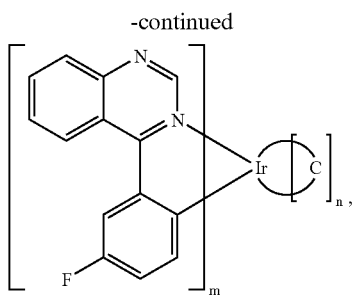
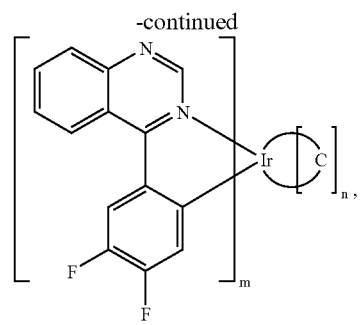
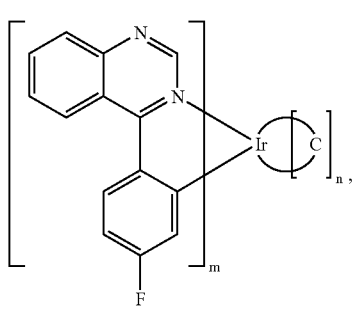
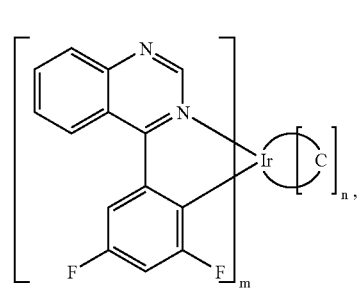
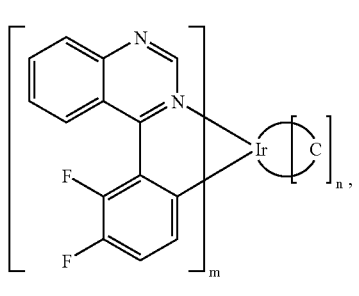
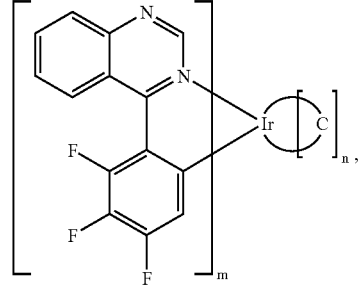
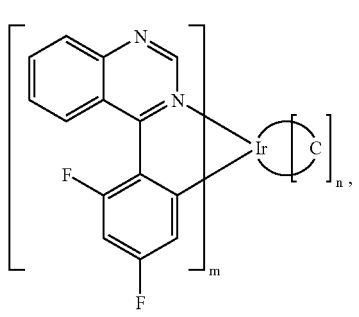
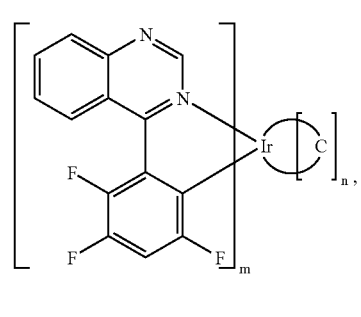
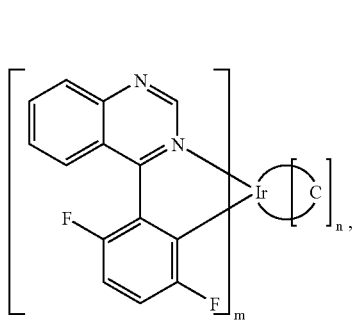
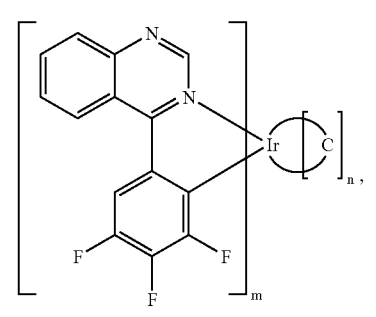

(2) 4-phenyl thieno[2,3-d]pyrimidine coordination group:

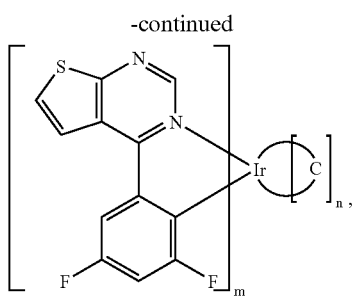
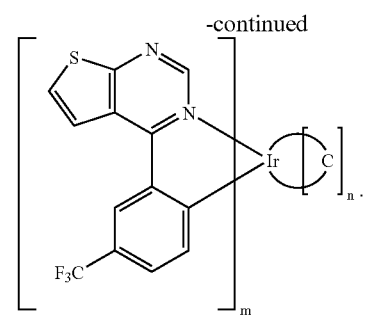
(3) 4-phenyl thieno[3,2-d]pyrimidine coordination group:
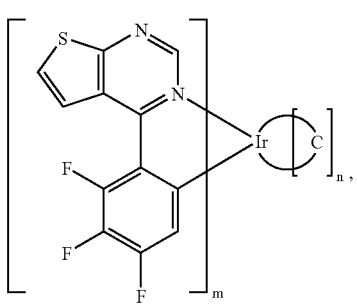
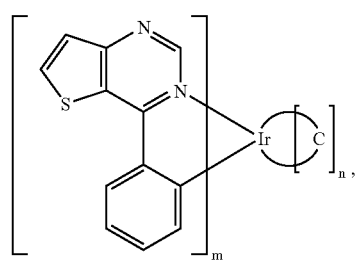
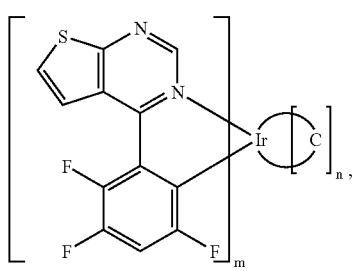
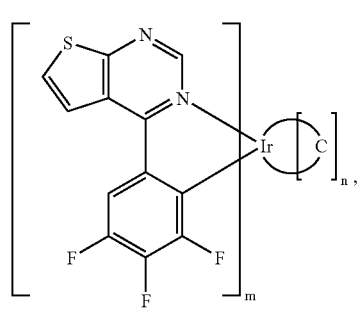
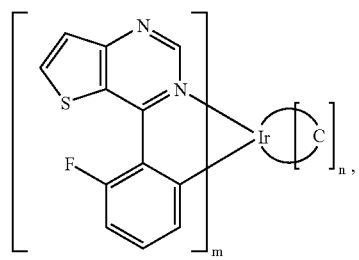
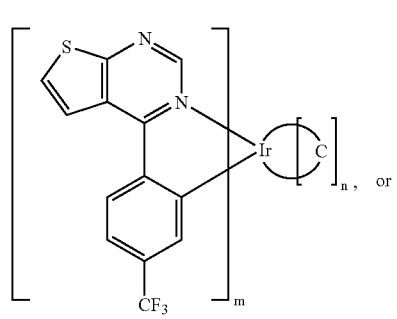, or
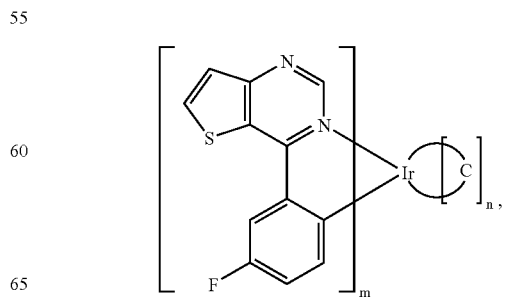, -continued
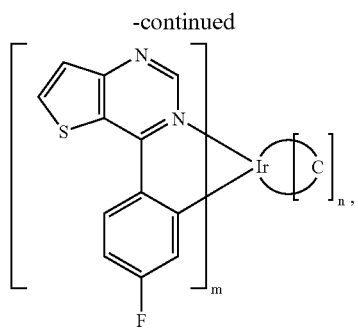
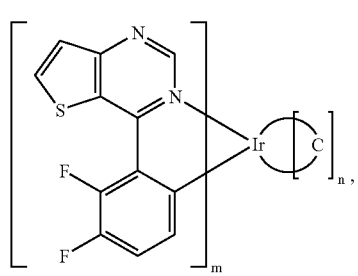
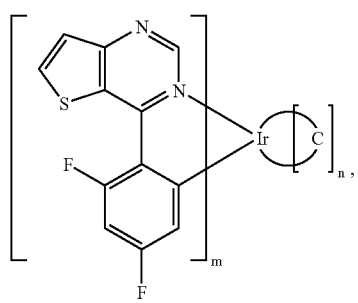
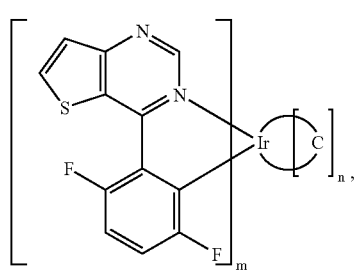
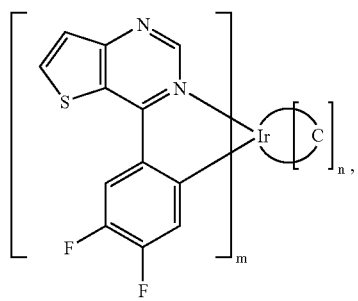
-continued
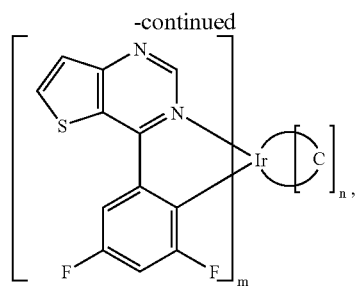
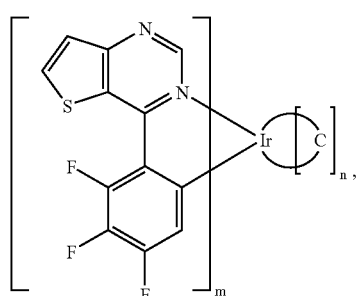
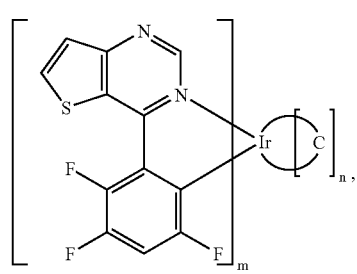
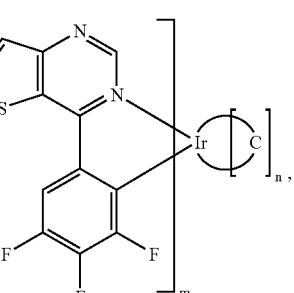
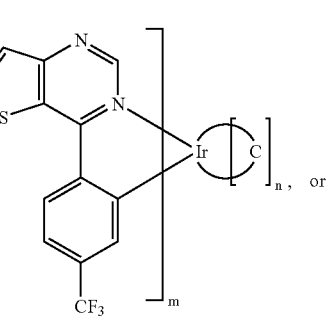

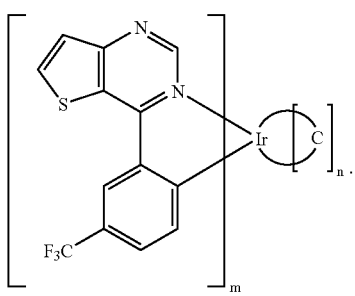

In the forgoing complexes, C is an acetyl acetone group

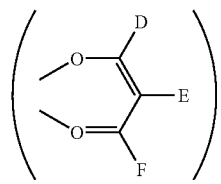

or picolinic acid group

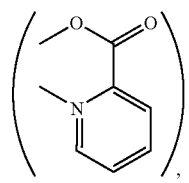

and D, E, and F are the same or different and comprise H, halogen atoms, trifluoromethyl, $C_{1-20}$ alkyl, $C_{1-20}$ alkyl halide, $C_{3-10}$ aryl, or $C_{3-20}$ heterocyclic ring containing O, N, or S, such as methyl, ethyl, isopropyl, sec-butyl, tert-butyl, phenyl, thiophenyl, benzothiophenyl, furanyl, napthalenyl, or pyridinyl. Additionally, m is 1~3, n is 0~3, and m+n=3.

The compound of formula (I) is prepared as follows. First, a coordination compound such as phenyl quinazoline or phenyl thienopyrimidine is prepared by general synthesis. Next, the coordination compound, a metal halide, solvent, and deionized water are added to a flask with thermal reflux for about 16~20 hours. The metal halide may be $IrCl_3 \cdot H_2O$, and the solvent may be ethylene glycol ethyl ether. After cooling to room temperature and filtration, collected solids are washed with a small quantity of solvent such as methanol. An organometallic dimer is prepared after drying. Next, the organometallic dimmer, a salt such as $Na_2CO_3$, a bidentate compound, and solvent such as ethylene glycol ethyl ether, are added to a flask with thermal reflux for about 16~20 hours. The bidentate compound comprises acetyl acetone or picolinic acid. After cooling to room temperature and filtration, collected solids are washed with a small quantity of solvent such as methanol. An organometallic complex (formula (I)) containing two coordination groups and a bidentate group (n=1) is prepared after drying. Another organometallic complex without bidentate groups (n=0) is prepared as follows. First, the foregoing organometallic complex containing two coordination groups and a bidentate group (n=1), a coordination compound, and solvent such as glycerol, are added to a flask with thermal reflux at 150~200° C. for about 6~10 hours. After cooling to room temperature and filtration, collected solids are washed with a small quantity of solvent such as methanol. An organometallic complex containing three coordination groups (n=0) is prepared after drying.

Original hydrogen atoms in a benzene ring are replaced by fluorine atoms. The modified complex structure provides several advantages, for example, high luminescent efficiency due to low-frequency vibrations of C—F bonds, effectively avoiding excited radiationless decay, low evaporation temperature, less self-quenching by alteration of stack structures of molecules, high electron mobility, and altered light color of red phosphorescent organic electroluminescent material by modification of HOMO-LUMO energy levels with fluoridized molecules.

Due to strong spin-orbital coupling, electrons in a singlet excited state of a $d^6$ Ir complex may easily migrate to a triplet excited state by Metal to Ligand Charge Transfer (MLCT) and hybrid π-π* coordination orbits, resulting in increased phosphorescent luminescent efficiency. Emission wavelength of the phosphorescent complex appears in a red light region of about 600~660 nm. Additionally, the invention provides a more simple synthesis of the novel red luminescent material.

The invention also provides an organic electroluminescent device comprising a pair of electrodes and an organic electroluminescent layer installed therebetween, utilizing the disclosed organometallic complex as formula (I).

The organic electroluminescent layer comprises an emitting layer comprising the disclosed organometallic complex used as a red luminescent dopant. Hosts of the emitting layer comprise CBP, TCTA, CzTT, TPBI, TAZ, BAlq, MCP, UGHI, UGH2, or UGH3. The organic electroluminescent layer further comprises a hole transport layer, a hole blocking layer, an electron transport layer, or a buffer layer. The hole transport layer comprises HTM2, TPD, NPB, PPD, TBPB, spiro-TAD, spiro-NPB, TPTE2, TPTE1, NTPA, or DNPD. The hole blocking layer comprises BPhen BCP, BAlq, CF—X, TAZ, or CF—Y. The electron transport layer comprises t-Bu-PBD, $Alq_3$, BeBq, TAZ, $Almq_3$, BAlq, or TPBI. The buffer layer may comprise LiF or $Li_2O$. The foregoing abbreviations represent the following structures.

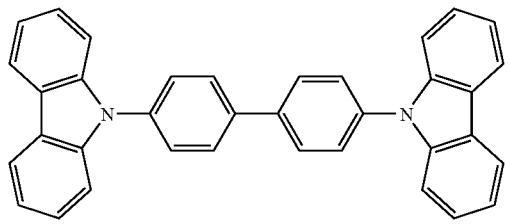
CBP
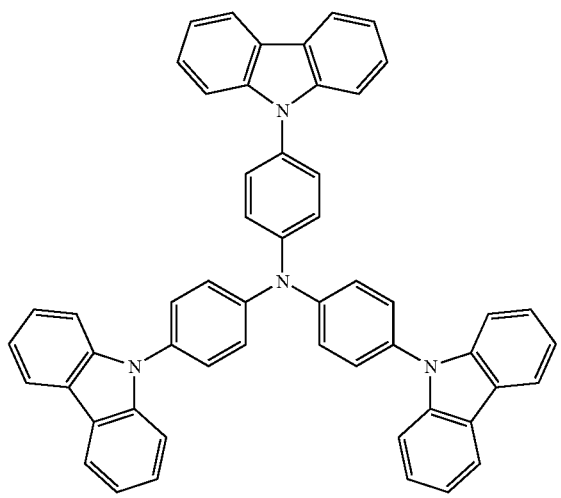
TCTA
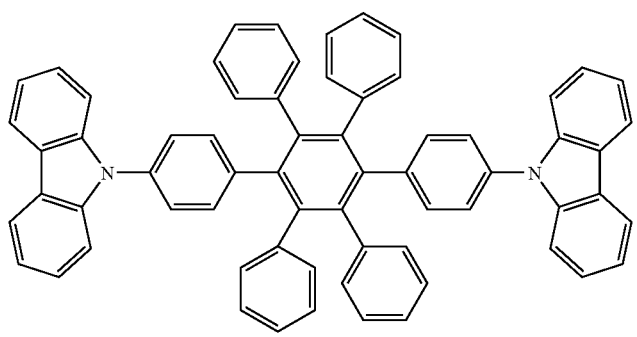
CzTT
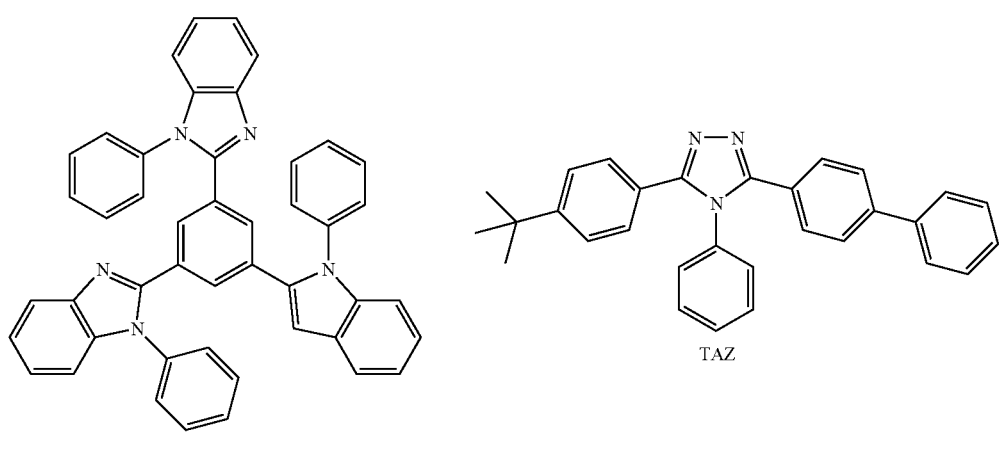
TPBI
TAZ

-continued
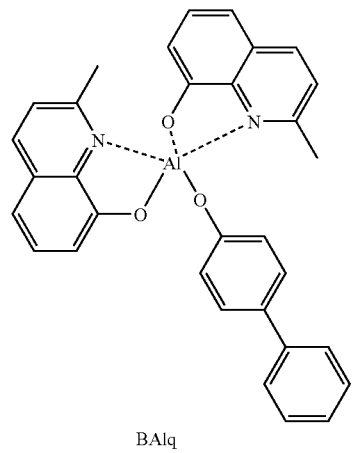
BAlq
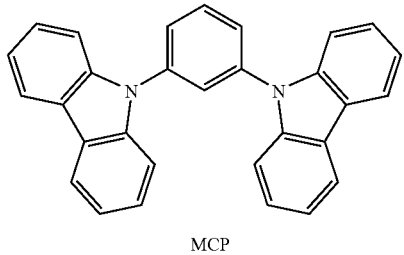
MCP
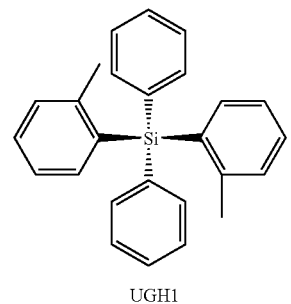
UGH1
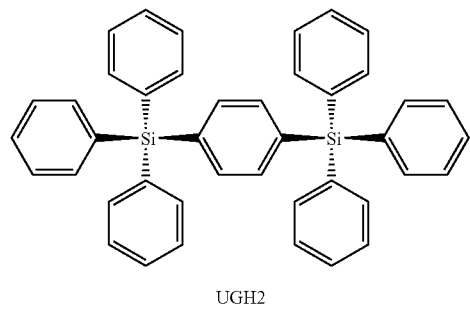
UGH2
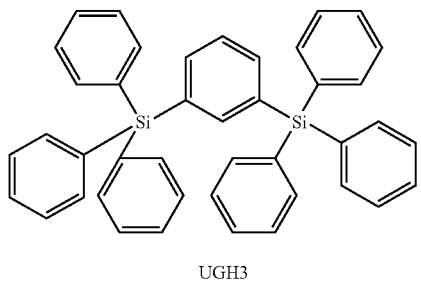
UGH3
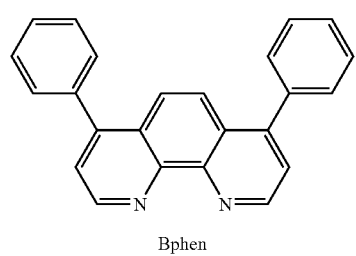
Bphen
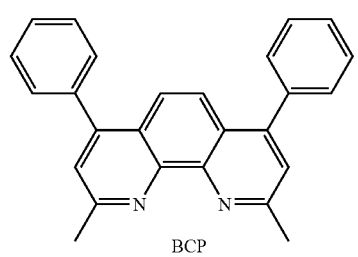
BCP
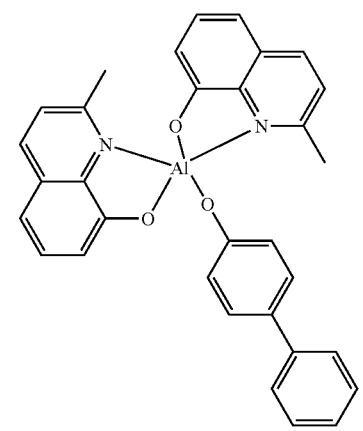
BAlq -continued
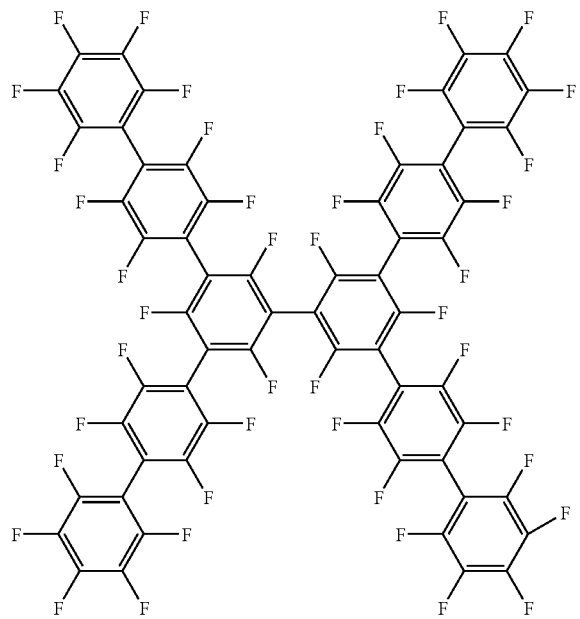
CF-X
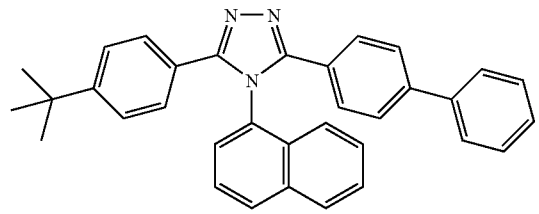
TAZ
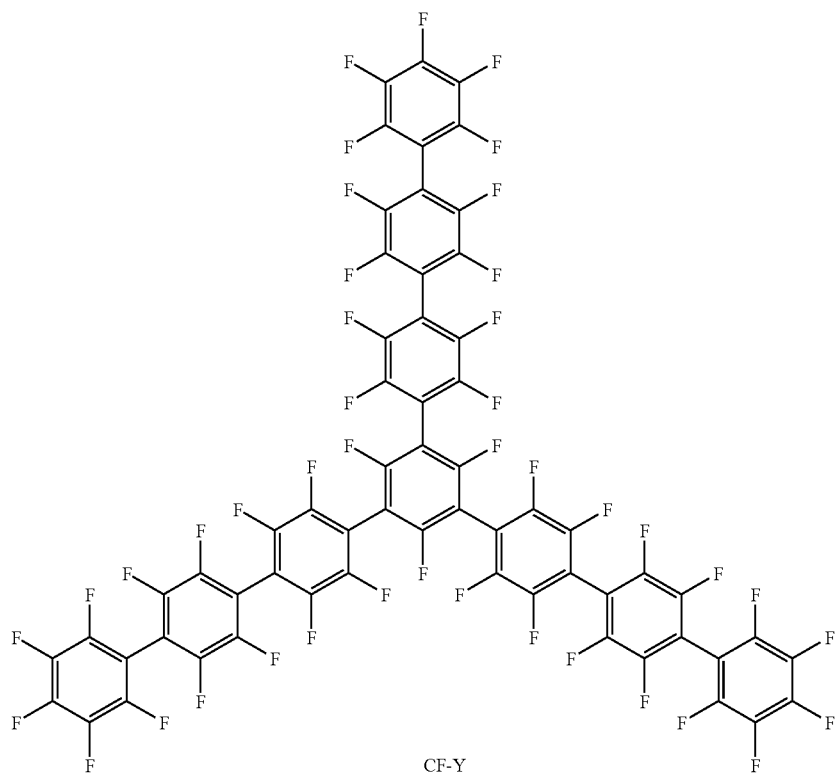
CF-Y -continued
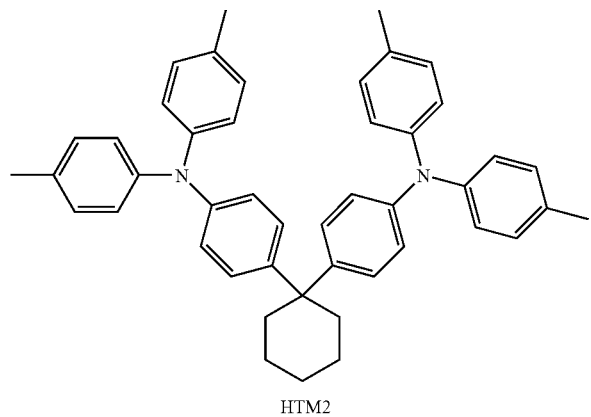
HTM2
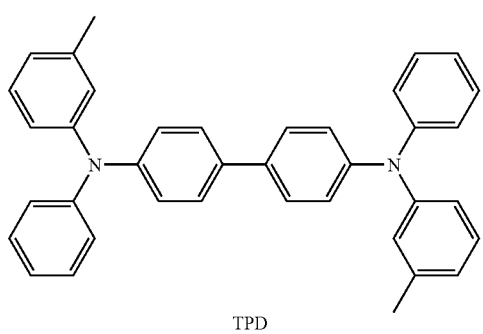
TPD
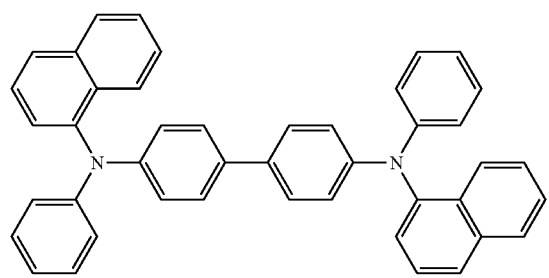
NPB
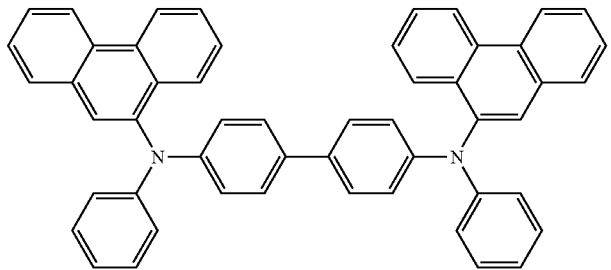
PPD
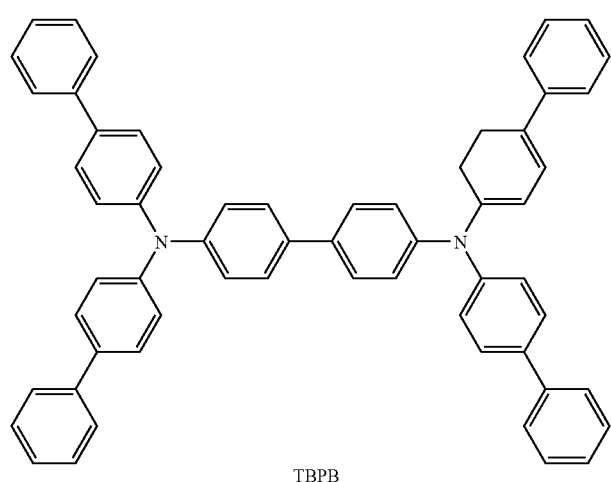
TBPB
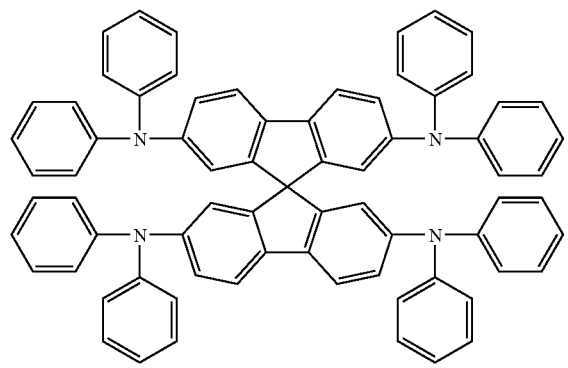
spiro-TAD
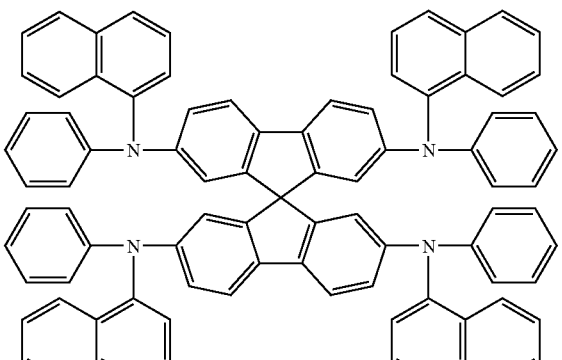
spiro-NPB -continued
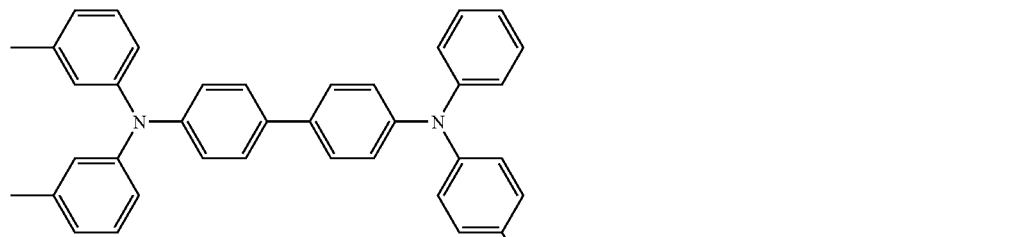
TPTE2
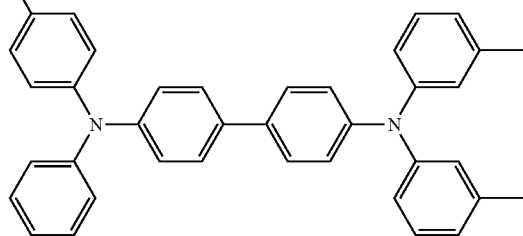
TPTE1
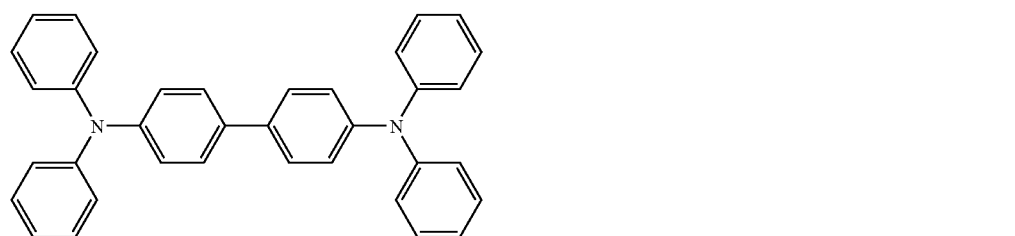
NTPA -continued
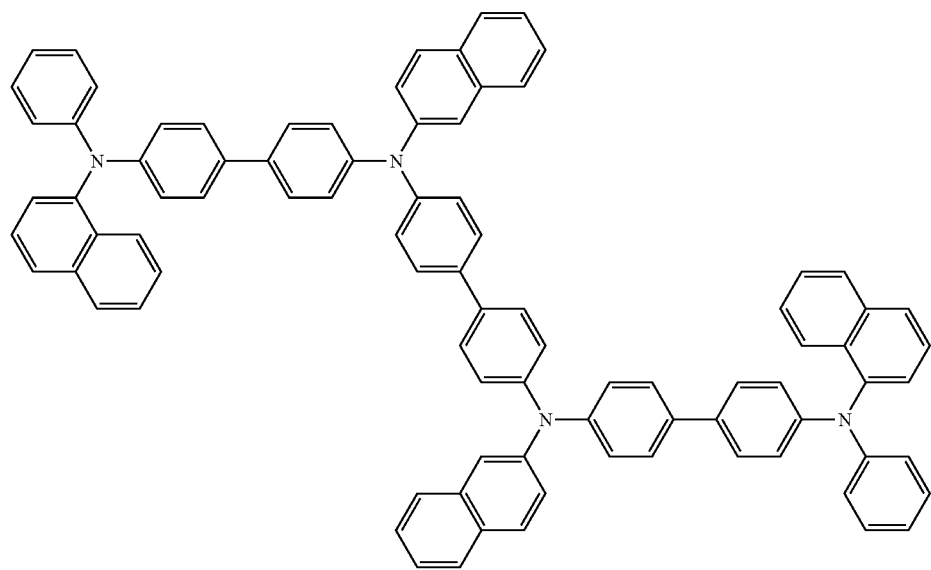
DNPD
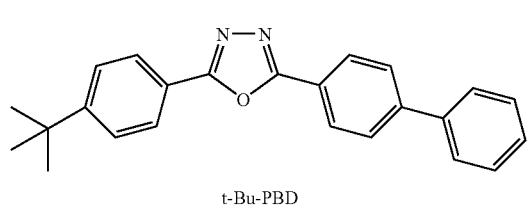
t-Bu-PBD
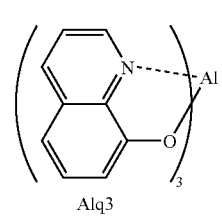
Alq3
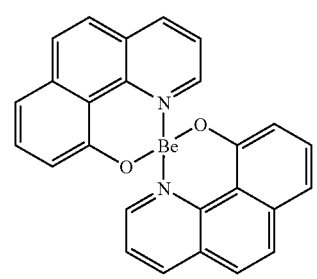
BeBq
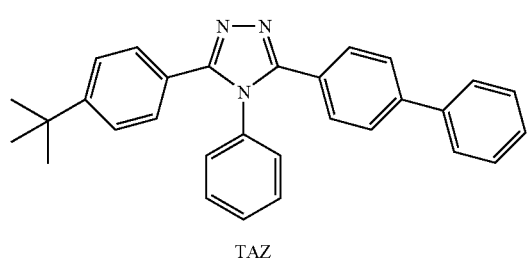
TAZ
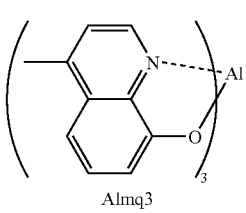
Almq3
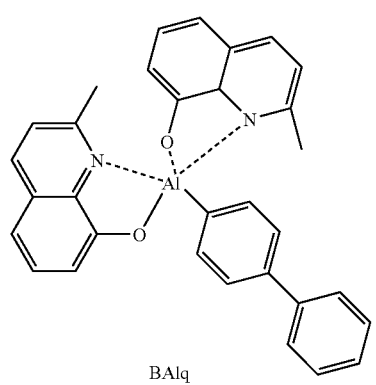
BAlq
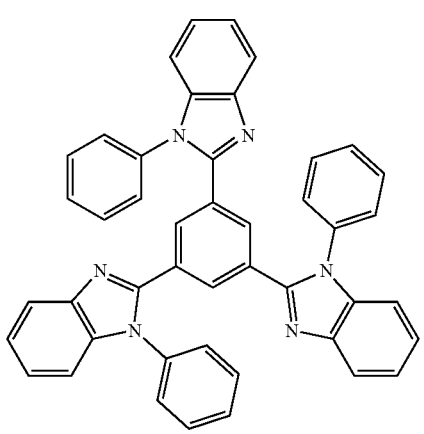
TPBI A method of fabricating an organic electroluminescent device is further provided. An anode is provided on a substrate and a hole transport layer is evaporated on the anode to a thickness of about 400~600 Å. A Ir complex (dopant) and host are then co-evaporated on the hole transport layer to form an emitting layer at a thickness of about 150~250 Å, with dopant/host volume ratio about 4~8%. Next, a hole blocking layer is evaporated on the emitting layer to a thickness of about 100~200 Å. An electron transport layer is evaporated on the hole blocking layer to a thickness of about 150~250 Å. A buffer layer is evaporated on the electron transport layer to a thickness of about 5~10 Å. Finally, a cathode is evaporated on the buffer layer to a thickness of about 1000~1400 Å.

The organic electroluminescent device has luminescent efficiency of about 1.5~6.51 lm/W, brightness of about 3.5~15.5 cd/A, a luminescent wavelength of about 600~660 nm, a CIEx value of about 0.66~0.70, and a CIEy value of about 0.30~0.33.

EXAMPLES

Example 1

Preparation of Compound 1

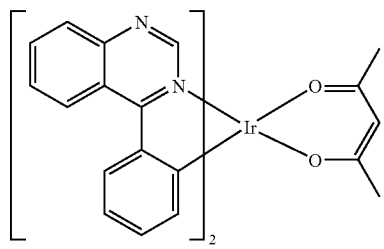

(1) 8 g 2-aminobenzophenone, 91 g formamide, and 25 g formic acid were added to a 250 ml flask and stirred at 150° C. for 2 hours. After returning to room temperature, 200 ml deionized water was added and filtered. Collected solids were then washed with a small quantity of deionized water and dried. 6.3 g yellow compound 1a was finally prepared with yield of 74% after re-crystallization with ethanol. The melting point thereof was 100~101° C. and its $^1$H-NMR (CDCl$_3$) data were 9.42 (1H, s, 2-H) and 8.28-7.15 (9H, m, ArH). The reaction according to step (1) was

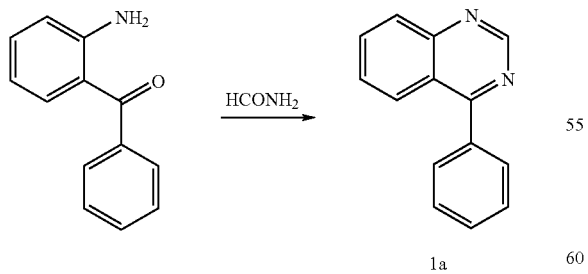

(2) 4 g compound 1a, 2 g IrCl$_3$*H$_2$O, 60 ml ethylene glycol ethyl ether, and 20 ml deionized water were added to a 150 ml flask under nitrogen gas with thermal reflux for 18 hours. After returning to room temperature and filtration, collected solids were then washed with a small quantity of methanol. After drying, 3.2 g yellow compound 1b was finally prepared with yield of 76%. The reaction according to step (2) was

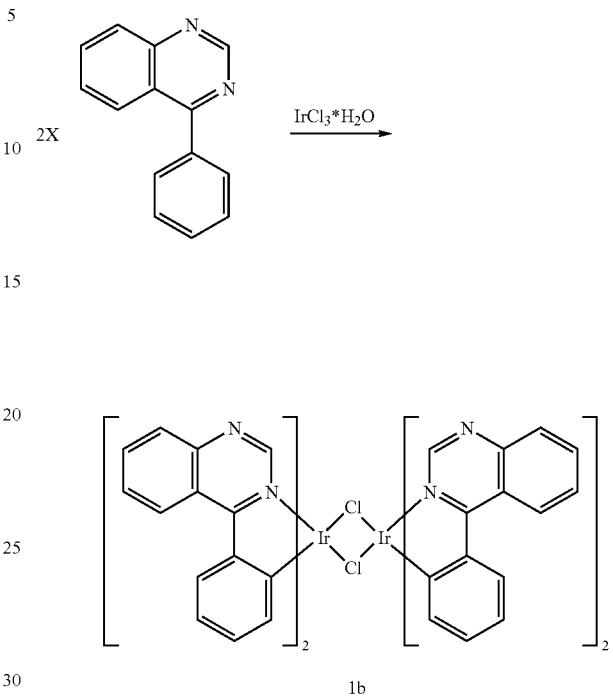

(3) 3.2 g compound 1b, 2.7 g Na$_2$CO$_3$, 5 ml acetyl acetone, and 120 ml ethylene glycol ethyl ether were added to a 250 ml flask under nitrogen gas with thermal reflux for 18 hours. After returning to room temperature and filtration, collected solids were then washed with a small quantity of methanol. After drying, 2.8 g yellow compound 1 was finally prepared with yield of 89%. The reaction according to step (3) was

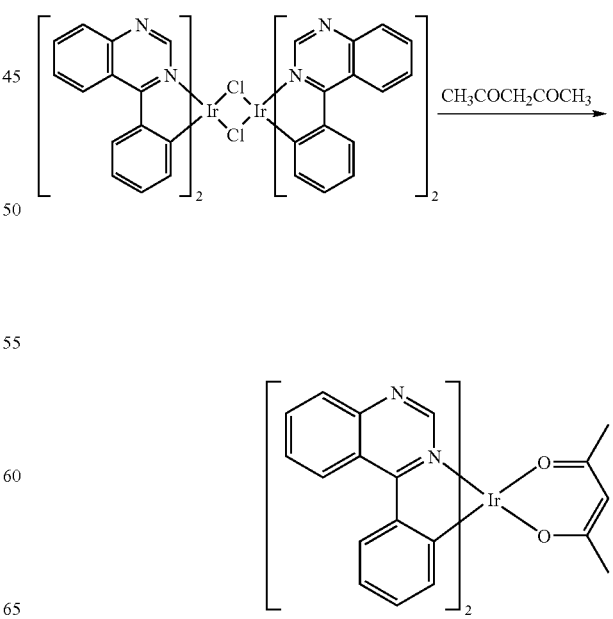

Example 2

Preparation of Compound 2

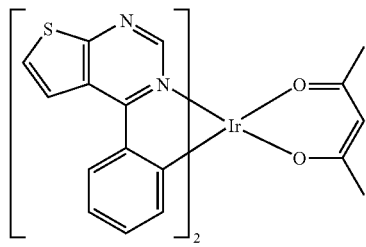

(1) 8 g 2-amino-thiophen-3-yl-phenyl-methanone, 91 g formamide, and 25 g formic acid were added to a 250 ml flask and stirred at 150° C. for 2 hours. After returning to room temperature, 200 ml deionized water was added and filtered. Collected solids were then washed with a small quantity of deionized water and dried. 5.3 g yellow compound 2a was finally prepared with yield of 62% after re-crystallization with ethanol. The reaction according to step (1) was

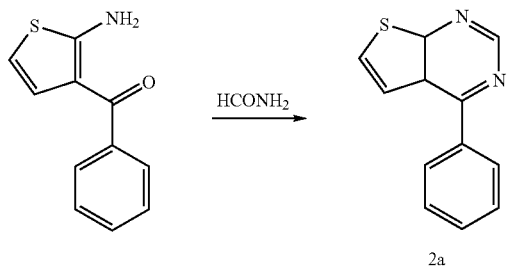

2a (2) 5.3 g compound 2a, 2.5 g $IrCl_3 \cdot H_2O$, 90 ml ethylene glycol ethyl ether, and 30 ml deionized water were added to a 250 ml flask under nitrogen gas with thermal reflux for 18 hours. After returning to room temperature and filtration, collected solids were then washed with a small quantity of methanol. After drying, 4.2 g yellow compound 2b was finally prepared with yield of 78%. The reaction according to step (2) was

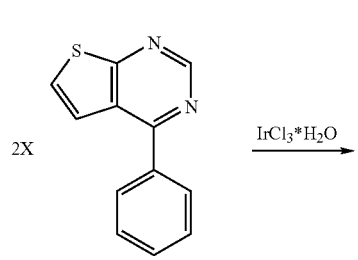

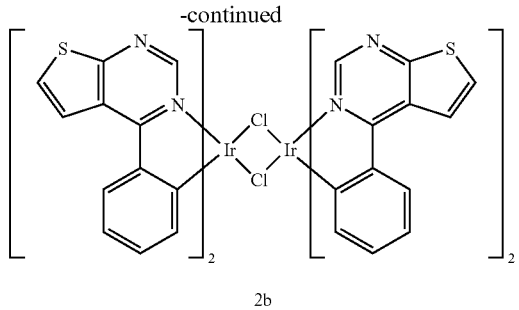

2b (3) 4.2 g compound 2b, 3.5 g $Na_2CO_3$, 6.5 ml acetyl acetone, and 160 ml ethylene glycol ethyl ether were added to a 250 ml flask under nitrogen gas with thermal reflux for 18 hours. After returning to room temperature and filtration, collected solids were then washed with a small quantity of methanol. After drying, 2.5 g yellow compound 2 was finally prepared with yield of 65%. The reaction according to step (3) was

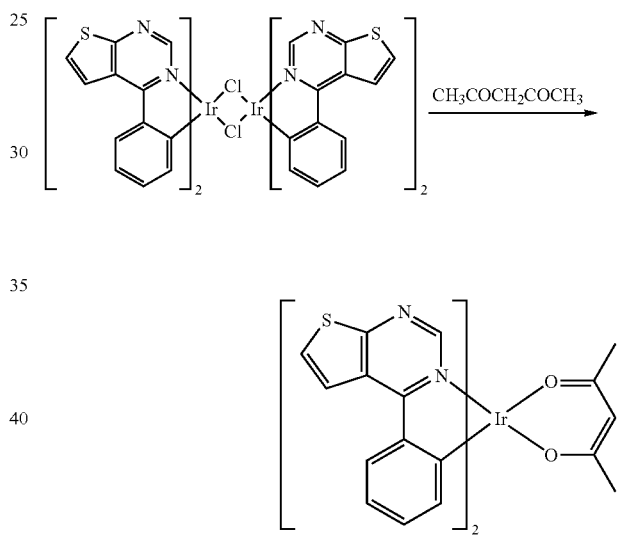

Example 3

Preparation of Compound 3

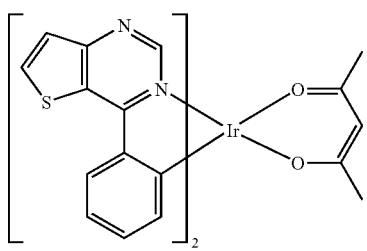

(1) 7 g 4-chlorothieno[3,2-d]pyrimidine, 5.6 g phenyl boric acid, and 0.14 g PPh₃ were added to a 250 ml flask under nitrogen gas. 120 ml $K_2CO_3$ (2M) and 80 ml 1,2-dimethoxy ethane (DME) were then added and heated to 60° C. Next, 0.3 g Pd(OAc)₂ was added with thermal reflux for 8 hours. After returning to room temperature, organo-layer was extracted by ethyl acetate. Remaining water in the organo-layer was then removed by adding MgSO₄. Finally, collected solids were purified by a silica gel chromatographic column (ethyl acetate:n-butane=1:4) to form 7.2 g white compound 3a with yield of 76%. The reaction according to step (1) was

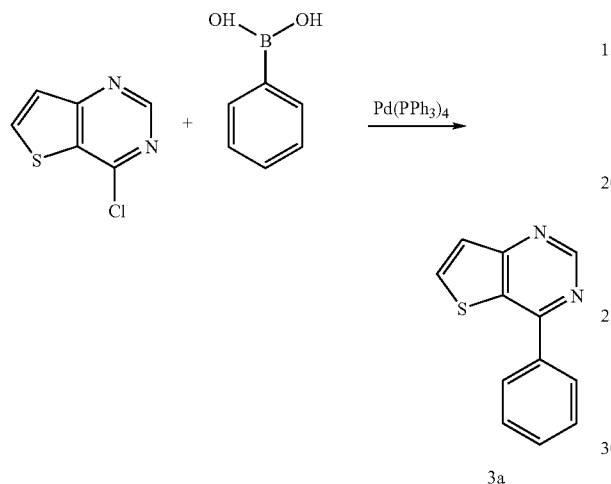

3a (2) 5 g compound 3a, 2.4 g IrCl₃*H₂O, 90 ml ethylene glycol ethyl ether, and 30 ml deionized water were added to a 250 ml flask under nitrogen gas with thermal reflux for 18 hours. After returning to room temperature and filtration, collected solids were then washed with a small quantity of methanol. After drying, 3.8 g yellow compound 3b was finally prepared with yield of 61%. The reaction according to step (2) was

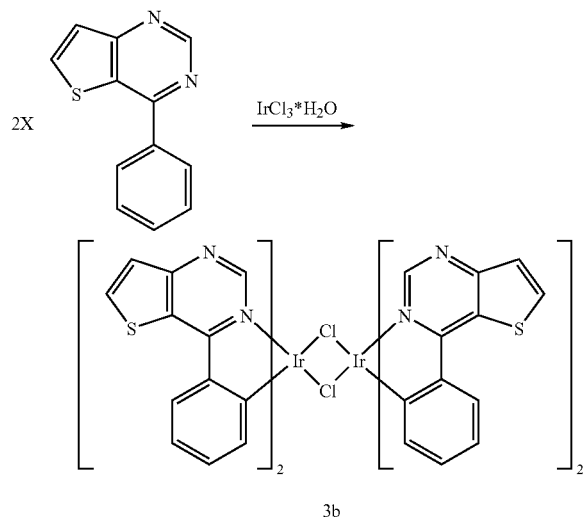

3b (3) 3.8 g compound 3b, 3.2 g Na₂CO₃, 6 ml acetyl acetone, and 150 ml ethylene glycol ethyl ether were added to a 250 ml flask under nitrogen gas with thermal reflux for 18 hours. After returning to room temperature and filtration, collected solids were then washed with a small quantity of methanol. After drying, 2 g yellow compound 3 was finally prepared with yield of 51%. The reaction according to step (3) was

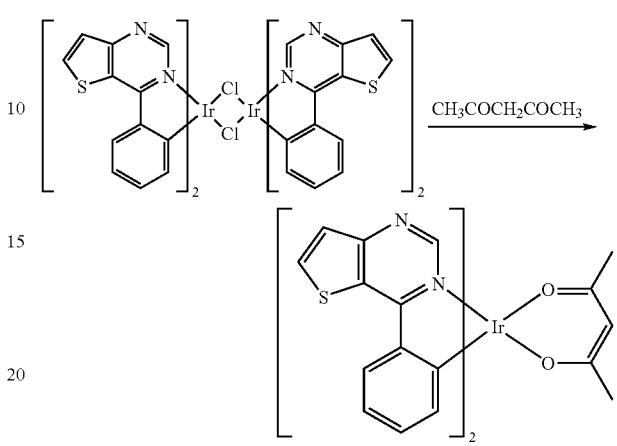

Example 4

Fabrication of Organic Electroluminescent Device

Referring to FIG. 1, a method of fabricating an organic electroluminescent device is disclosed according to the following example, in which an ITO anode 100 was provided on a substrate and washed with cleaning agent and deionized water. After drying, NPB was evaporated on the ITO anode 100 to form a hole transport layer 110 at a thickness of 500 Å. Ir complex (compound 1, dopant) and CBP (host) were then co-evaporated on the hole transport layer 110 to form an emitting layer 120 at a thickness of 200 Å. The dopant/host volume ratio thereof was 6%. Next, BCP was evaporated on the emitting layer 120 to form a hole blocking layer 130 at a thickness of 150 Å. Next, Alq₃ was evaporated on the hole blocking layer 130 to form an electron transport layer 140 at a thickness of 200 Å. Next, LiF was evaporated on the electron transport layer 140 to form a buffer layer 150 at a thickness of 5 Å. Finally, Al was evaporated on the buffer layer 150 to form a cathode 160 at a thickness of 1200 Å.

Various brightness, luminescent efficiency, wavelengths, and CIE values between the devices utilizing compound 1, 2, and 3, respectively, provided by the invention and the devices utilizing related luminescent materials, such as PtOEP, Btp2Ir (acac), and Piq2Ir(acac) were compared as shown in Table 1.

TABLE 1

| materials | Brightness (cd/A) | Luminescent efficiency (lm/W) | Wavelength (nm) | CIE (x, y) values |
|---|---|---|---|---|
| Compound 1 | 3.75 | 1.82 | 648 | (0.70, 0.30) |
| Compound 2 | 15.02 | 6.10 | 600 | (0.57, 0.42) |
| Compound 3 | 14.01 | 5.31 | 605 | (0.59, 0.40) |
| PtOEP | 2.22 | 1.08 | 650 | (0.69, 0.30) |
| Btp2Ir (acac) | 3.40 | 1.65 | 620 | (0.62, 0.35) |
| Piq2Ir (acac) | 4.33 | 2.10 | 624 | (0.67, 0.32) |

The results indicate that the red organic electroluminescent material of the invention provides better brightness, luminescent efficiency, and CIE values. Additionally, synthesis thereof is also simple, meeting economic benefits.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organometallic complex selected from the group consisting of

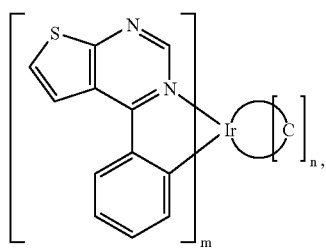

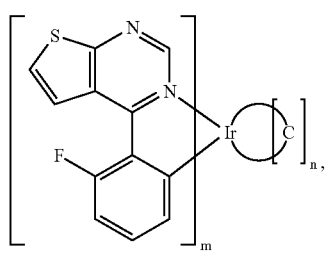

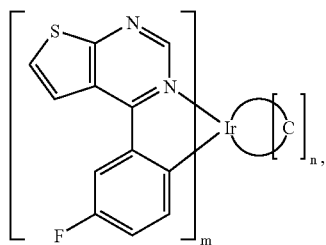

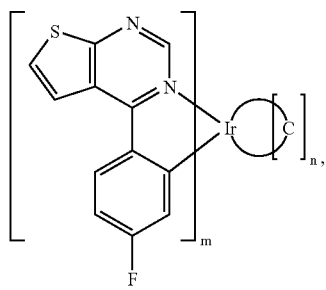

-continued

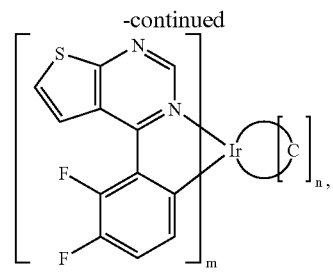

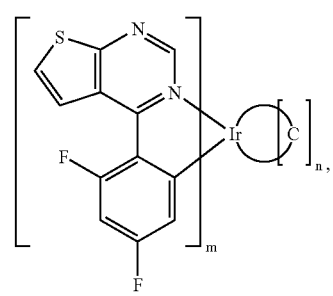

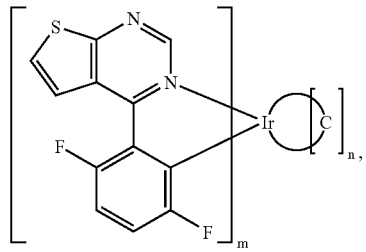

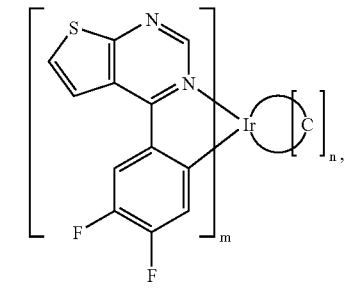

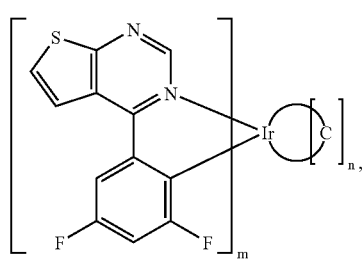

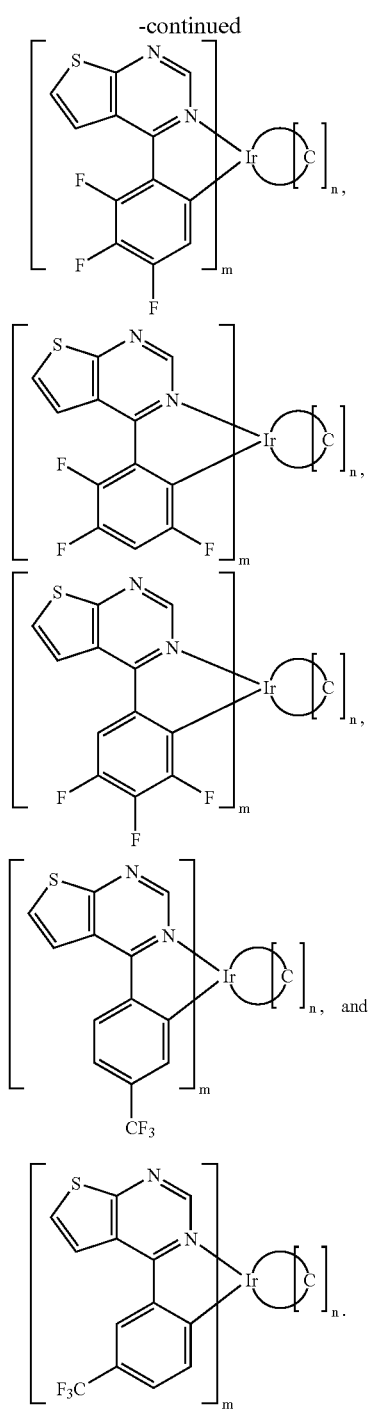

wherein C is an acetyl acetone group

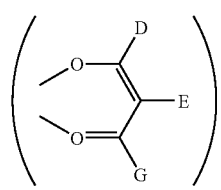

or picolinic acid group

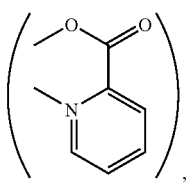

m is 1-3, n is 0-3 and m+n=3, wherein D, E and G are the same or different and selected from the group consisting of H, halogen atoms, trifluoromethyl, $C_{1-20}$ alkyl, $C_{1-20}$ alkyl halide, $C_{3-10}$ aryl and $C_{3-20}$ heterocyclic ring containing O, N or S.

2. The organometallic complex as claimed in claim 1, wherein D, E, and G are selected from the group of methyl, ethyl, isopropyl, sec-butyl, phenyl, thiophenyl, benzothiophenyl, furanyl, napthalenyl, and pyridinyl.

3. The organometallic complex as claimed in claim 1, wherein the organometallic complex is a luminescent material.

4. The organometallic complex as claimed in claim 1, wherein the organometallic complex is a red phosphorescent dopant.

5. An organic electroluminescent device, comprising:
a pair of electrodes; and
an organic electroluminescent layer installed between the electrodes, comprising an organometallic complex as claimed in claim 1.

6. The organic electroluminescent device as claimed in claim 5, wherein the organic electroluminescent layer comprises an emitting layer comprising the organometallic complex.

7. The organic electroluminescent device as claimed in claim 6, wherein the organometallic complex is a red luminescent dopant.

8. The organic electroluminescent device as claimed in claim 5, wherein the organic electroluminescent layer comprises a hole transport layer, a hole blocking layer, an electron transport layer, or a buffer layer.

9. The organic electroluminescent device as claimed in claim 5, wherein the organic electroluminescent device has a luminescent efficiency of about 1.5~6.51 lm/W.

10. The organic electroluminescent device as claimed in claim 5, wherein the organic electroluminescent device has a brightness of about 3.5~15.5 cd/A.

11. The organic electroluminescent device as claimed in claim 5, wherein the organic electroluminescent device has a luminescent wavelength of about 600~660 nm.

12. The organic electroluminescent device as claimed in claim 5, wherein the organic electroluminescent device has a CIEx value of about 0.66~0.70 and a CIEy value of about 0.30~0.33.

13. The organic electroluminescent device as claimed in claim 5, wherein the organic electroluminescent device has an internal quantum efficiency of about 25~100%.

14. An organometallic complex selected from the group consisting of
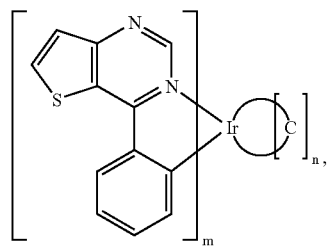
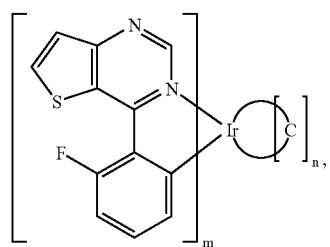
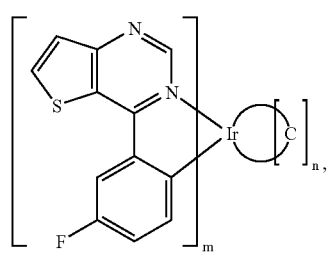
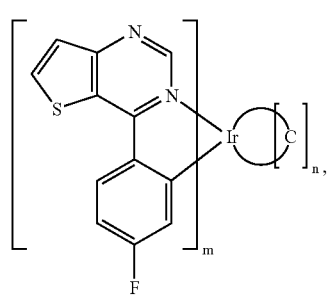
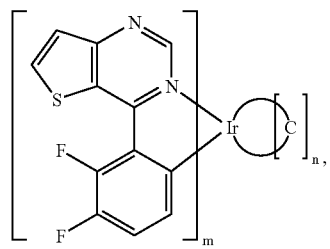
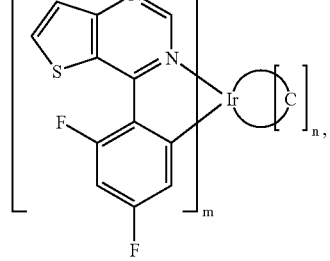
-continued
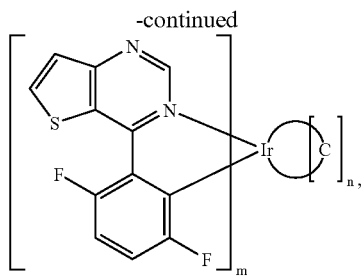
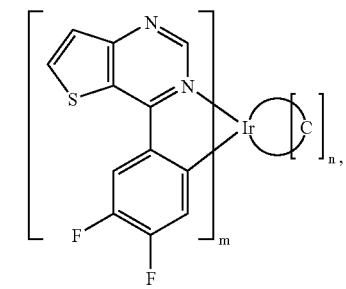
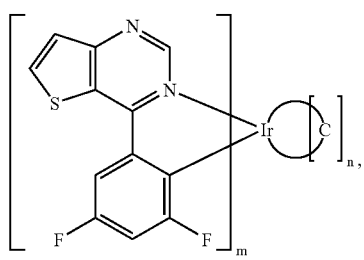
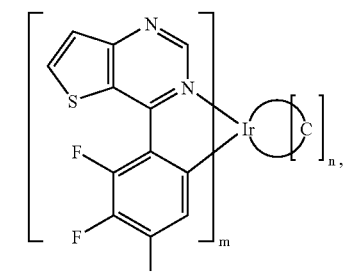
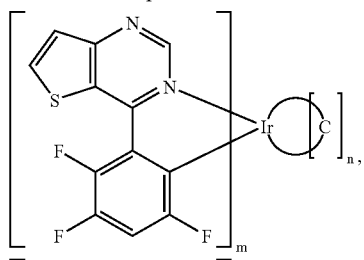
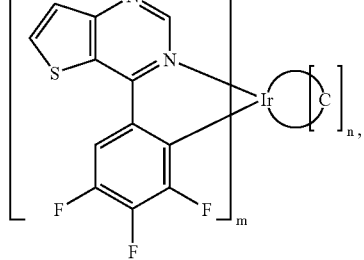

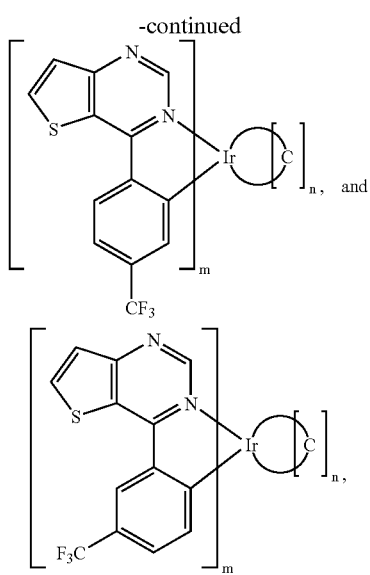

wherein C is an acetyl acetone group

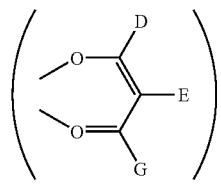

or picolinic acid group

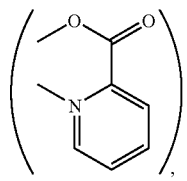

m is 1-3, n is 0-3 and m+n=3, wherein D, E and G are the same or different and selected from the group consisting of H, halogen atoms, trifluoromethyl, $C_{1-20}$ alkyl, $C_{1-20}$ alkyl halide, $C_{3-10}$ aryl and $C_{3-20}$ heterocyclic ring containing O N or S.

15. The organometallic complex as claimed in claim 14, wherein D, E, and G are selected from the group consisting of methyl, ethyl, isopropyl, sec-butyl, tert-butyl, phenyl, thiophenyl, benzothiophenyl, furanyl, napthalenyl and pyridinyl.

16. The organometallic complex as claimed in claim 14, wherein the organometallic complex is a luminescent material.

17. The organometallic complex as claimed in claim 14, wherein the organometallic complex is a red phosphorescent dopant.

18. An organic electroluminescent device, comprising:
a pair of electrodes; and
an organic electroluminescent layer installed between the electrodes, comprising an organometallic complex as claimed in claim 14.

19. The organic electroluminescent device as claimed in claim 18, wherein the organic electroluminescent layer comprises an emitting layer comprising the organometallic complex.

20. The organic electroluminescent device as claimed in claim 19, wherein the organometallic complex is a red luminescent dopant.

21. The organic electroluminescent device as claimed in claim 18, wherein the organic electroluminescent layer comprises a hole transport layer, a hole blocking layer, an electron transport layer, or a buffer layer.

22. The organic electroluminescent device as claimed in claim 18, wherein the organic electroluminescent device has a luminescent efficiency of about 3.5~6.51 lm/W.

23. The organic electroluminescent device as claimed in claim 18, wherein the organic electroluminescent device has a brightness of about 3.5~15.5 cd/A.

24. The organic electroluminescent device as claimed in claim 18, wherein the organic electroluminescent device has a luminescent wavelength of about 600~660 nm.

25. The organic electroluminescent device as claimed in claim 18, wherein the organice electroluminescent device has a CIEx value of about 0.66~0.70 and a CIEy value of about 0.30~0.33.

26. The organinc electroluminescent device as claimed in clam 18, wherein the oganice electroluminescent device has an internal quantum efficiency of about 25~100%.

* * * * *